(12) United States Patent
Sayo et al.

(10) Patent No.: US 6,342,644 B1
(45) Date of Patent: Jan. 29, 2002

(54) METHOD FOR PRODUCING 1-MENTHOL

(75) Inventors: Noboru Sayo; Takaji Matsumoto, both of Kanagawa (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 09/849,306

(22) Filed: May 7, 2001

(30) Foreign Application Priority Data

May 10, 2000 (JP) ............................................ 12-137388

(51) Int. Cl.$^7$ .............................................. C07L 27/00
(52) U.S. Cl. ........................ 568/830; 568/350; 568/377
(58) Field of Search ................................ 568/350, 377, 568/830

(56) References Cited

U.S. PATENT DOCUMENTS 3,870,761 A * 3/1975 Pasedach

OTHER PUBLICATIONS

Solodar, "Asymmetric and Regioselective Hydrogenation of Piperitenone by Homogeneous Rhodium Complexes", J. Org. Chem., vol. 43, No. 9, p 1787–1789 (1978).

P. Le Maux et al, "Catalytic Asymmetric Syntheses. Part III. Asymmetric Hydrogenation of Piperitenone Catalysed by Chiral Ruthenium Hydrides: An Example of a Catalytic Kinetic Resolution",Tetrahedron vol. 44, No. 5, p 1409–1412 (1988).

Ohkuma et al, "Asymmetric Hydrogenation of Cyclic $\alpha$, $\beta$–Unsaturated Ketones to Chiral Allylic Alcohols", Synlett, May 1997, p 467–468.

* cited by examiner

Primary Examiner—Micahael L. Shippen
(74) Attorney, Agent, or Firm—Sughrue Mion, PLLC

(57) ABSTRACT

Provided is a method for the production of 1-menthol, which comprises hydrogenation of piperitenone with a transition metal complex of a specified optically active phosphine to produce pulegone, hydrogenation of the obtained pulegone with a ruthenium-phosphine-amine complex in the presence of base to obtain pulegol, and further hydrogenation of the pulegol with a transition metal catalyst.

11 Claims, No Drawings

METHOD FOR PRODUCING 1-MENTHOL

FIELD OF THE INVENTION

This invention relates to methods for the production of 1-menthol which is used as a medicament or perfume and of its intermediate pulegone.

BACKGROUND OF THE INVENTION

There are some reports on the hydrogenation reaction into pulegone from piperitenone which can be easily synthesized from mesityl oxide and methyl vinyl ketone. There are an example 1) reported by J. Solodar et al. in *J. Org. Chem.*, vol. 43, p. 1787, 1978, in which the hydrogenation is carried out using a Rh complex which uses cyclohexylanisylmethylphosphine as the ligand and an example 2) reported by P. L. Maux et al. in *Tetrahedron*, vol. 44, p. 1409, 1988, in which the hydrogenation is carried out using a diphenylneomenthylphosphine-Co complex.

Regarding reports on pulegol from pulegone, there is an example described by T. Ohkuma et al. in *Synlett*, p. 467, 1997, in which a catalyst system of (S)-BINAP-Ru-(S,S)-diphenylethylenediamine-KOH is used.

Regarding the synthesis of pulegone, the method 1) can synthesize it with a selectivity of about 90% but its optical purity is a low value of 33% ee, and DMF (dimethylformamide) is used in the reaction solvent, so that this method is not industrially applicable. Also, the method 2) can synthesize it only with a selectivity of 55% and an optical purity of 15% ee, so that they are not industrially applicable levels.

In addition, the ligand to be used in the synthesis of pulegol is a combination of (S)-BINAP and (S,S)-diphenylethylenediamine, and since optically active substances are used for both of them, this method has a problem of high catalyst cost.

SUMMARY OF THE INVENTION

The invention contemplates solving the illustrative problems shown in the following items 1) to 3).

1) Since there are three positions in piperitenone where hydrogenation can be effected, it is necessary for obtaining pulegone to increase position selectivity of hydrogenation. That is, it is necessary to select a catalyst, namely a ligand and a transition metal, which can attain superior selectivity and optical yield to those of conventionally used ligands including a monodentate phosphine such as cyclohexylanisylmethylphosphine, phenylanisylmethylphosphine or cyclohexyl-o-tert-butylphenylmethylphosphine and a bidentate phosphine such as DIPAMP: 1,2-bis[(o-methoxyphenyl)phenylphosphino]ethane or DIOP: 2,3-o-isopropylidene-2,3-dihydroxy-1,4-bis-(diphenylphosphino)butane, and to examine solvent systems and additives which exert influences thereon.

2) Regarding preparation of pulegol from pulegone, significant result is obtained by a prior art ruthenium-diamine-potassium hydroxide system, so that it is expected to obtain equivalent catalytic activity and selectivity by changing it to an inexpensive catalyst.

3) The method to obtain menthol by hydrogenating pulegol can be carried out using a heterogeneous hydrogenation catalyst, but concern has been directed toward the development of a catalyst system having more higher selectivity.

DETAILED DESCRIPTION OF THE INVENTION

The following describes the invention in detail.

The piperitenone to be used in the invention can be prepared by allowing mesityl oxide to react with methyl vinyl ketone in the presence of potassium hydroxide (cf. JP-B-57-47168; the term "JP-B" as used herein means an "examined Japanese patent publication") or by condensing mesityl oxide with 4-diethylamino-2-butanone.

In the invention, the 2-position olefin of piperitenone is hydrogenated as the first hydrogenation reaction. The reaction formula is shown below.

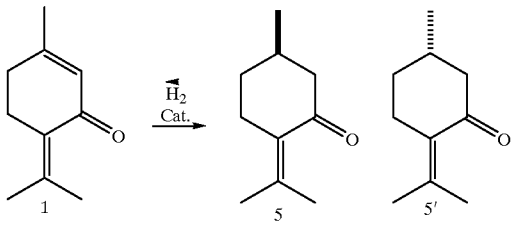

As the ligand to be used in the catalyst for hydrogenation of the 2-position olefin of piperitenone, there is an optically active phosphine represented by a general formula (2)

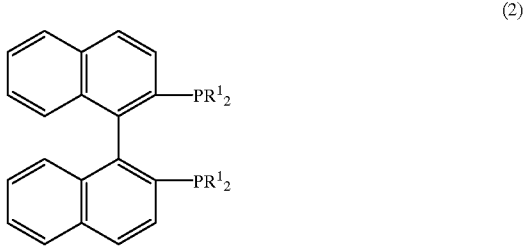

wherein $R^1$ represents an aryl group which may have a substituent group or a cycloalkyl group having from 3 to 8 carbon atoms.

In this general formula (2) of the present invention. $R^1$ is a phenyl group which may have a substitutent group, a naphthyl group which may have substitutent group or a cycloalkyl group having from 3 to 8 carbon atoms.

Examples of the substituents thereof include lower alkyl groups having 1 to 4 carbon atoms, such as methyl, ethyl, propyl, isopropyl, n-butyl, t-butyl, and isobutyl; halogen atoms such as fluorine, chlorine, and bromine; lower alkoxy groups having 1 to 4 carbon atoms, such as methoxy, ethoxy, propoxy, and butoxy; halogenated lower alkyl groups such as trifluoromethyl and trichloromethyl, and benzyloxy.

Preferred examples of $R^1$ include phenyl, 4-tolyl, 3-tolyl, 4-methoxyphenyl, 3,5-xylyl, 3,5-di-tert-butylphenyl, 4-methoxy-3,5-dimethylphenyl, 4-methoxy-3,5-di-tert-butylphenyl, naphthyl, cyclohexyl and cyclopentyl.

Examples of the optically active phosphine to be desirably used according to this general formula (2) include tertiary phosphines described in JP-A-61-63690 and JP-A-62-265293 (the term "JP-A" as used herein means an "unexamined published Japanese patent application"), and the following can be cited as illustrative examples.

2,2'-Bis(diphenylphosphino)-1,1'-binaphthyl (to be referred to as "BINAP" hereinafter), 2,2'-bis[di(p-tolyl)phosphino]-1,1'-binaphthyl (to be referred to as "Tol-BINAP" hereinafter), 2,2'-bis[di(3,5-xylyl)phosphino]-1,1'-binaphthyl (to be referred to as "DM-BINAP" hereinafter), 2,2'-bis[di(3,5-di-tert-butylphenyl)phosphino]-1,1'-binaphthyl (to be referred to as "(t-Bu)2-BINAP" hereinafter), 2,2'-bis[di(4-methoxy-3,5-dimethylphenyl)phosphino]-1,1'-binaphthyl (to be referred to as "DMM-BINAP" hereinafter), 2,2'-bis(dicyclohexylphosphino)-1,1'-binaphthyl (to be referred to as "Cy-BINAP" hereinafter), and 2,2'-bis(dicyclopentylphosphino)-1,1'-binaphthyl (to be referred to as "Cp-BINAP" hereinafter).

As another ligand to be used in the catalyst for the first hydrogenation reaction, there is an optically active phosphine represented by a general formula (3)

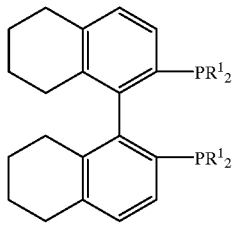

(3)

wherein $R^1$ represents an aryl group which may have a substituent group or a cycloalkyl group having from 3 to 8 carbon atoms.

In this general formula (3) of the present invention. $R^1$ is a phenyl group which may have a substitutent group, a naphthyl group which may have substitutent group or a cycloalkyl group having from 3 to 8 carbon atoms.

Examples of the substituents thereof include lower alkyl groups having 1 to 4 carbon atoms, such as methyl, ethyl, propyl, isopropyl, n-butyl, t-butyl, and isobutyl; halogen atoms such as fluorine, chlorine, and bromine; lower alkoxy groups having 1 to 4 carbon atoms, such as methoxy, ethoxy, propoxy, and butoxy; halogenated lower alkyl groups such as trifluoromethyl and trichloromethyl, and benzyloxy.

Preferred examples of $R^1$ include phenyl, 4-tolyl, 3-tolyl, 4-methoxyphenyl, 3,5-xylyl, 3,5-di-tert-butylphenyl, 4-methoxy-3,5-dimethylphenyl, 4-methoxy-3,5-di-tert-butylphenyl, naphthyl, cyclohexyl and cyclopentyl.

Examples of the optically active phosphine to be desirably used according to this general formula (3) include tertiary phosphines described in JP-A-4-139140 (the term "JP-A" as used herein means an "unexamined published Japanese patent application"), and the following can be cited as illustrative examples.

2,2'-Bis{diphenylphosphino}-5,5'6,6',7,7',8,8'-octahydrobinaphthyl (to be referred to as "H₈-BINAP" hereinafter), 2,2'-bis{di-p-tolylphosphino}-5,5'6,6',7,7',8,8'-octahydrobinaphthyl (to be referred to as "p-Tol-H₈-BINAP" hereinafter), 2,2'-bis{di-(3,5-xylyl)phosphino}-5,5'6,6',7,7',8,8'-octahydrobinaphthyl (to be referred to as "DM-H₈-BINAP" hereinafter), and 2,2'-bis{di-(4-methoxy-3,5-dimethylphenyl)phosphino}-5,5'6,6',7,7',8,8'-octahydrobinaphthyl (to be referred to as "DMM-H₈-BINAP" hereinafter).

As still another ligand to be used in the catalyst for the first hydrogenation reaction, there is an optically active phosphine represented by a general formula (4)

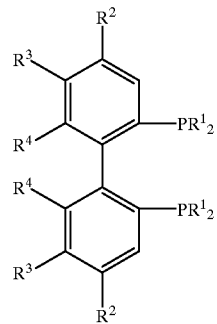

(4)

wherein R represents an aryl group which may have a substituent group or a cycloalkyl group having from 3 to 8 carbon atoms, $R^2$ represents hydrogen atom or a lower alkyl group having from 1 to 4 carbon atoms, $R^3$ represents hydrogen atom methyl group, methoxy group or a halogen atom, and $R^4$ represents methyl group or methoxy group, or $R^3$ and $R^4$ may be coupled together to form methylenedioxy group.

In this general formula (4) of the present invention. $R^1$ is a phenyl group which may have a substitutent group, a naphthyl group which may have substitutent group or a cycloalkyl group having from 3 to 8 carbon atoms.

Examples of the substituents thereof include lower alkyl groups having 1 to 4 carbon atoms, such as methyl, ethyl, propyl, isopropyl, n-butyl, t-butyl, and isobutyl; halogen atoms such as fluorine, chlorine, and bromine; lower alkoxy groups having 1 to 4 carbon atoms, such as methoxy, ethoxy, propoxy, and butoxy; halogenated lower alkyl groups such as trifluoromethyl and trichloromethyl, and benzyloxy.

Preferred examples of $R^1$ include phenyl, 4-tolyl, 3-tolyl, 4-methoxyphenyl, 3,5-xylyl, 3,5-di-tert-butylphenyl, 4-methoxy-3,5-dimethylphenyl, 4-methoxy-3,5-di-tert-butylphenyl, naphthyl, cyclohexyl and cyclopentyl.

Examples of the optically active phosphine to be desirably used according to this general formula (4) include tertiary phosphines described in JP-A-11-269,185 (the term "JP-A" as used herein means an "unexamined published Japanese patent application"), and the following can be cited as illustrative examples.

((5,6),(5',6')-Bis(methylenedioxy)biphenyl-2,2'-diyl)bis(diphenylphosphine) (to be referred to as "SEGPHOS" hereinafter), ((5,6),(5',6')-bis(methylenedioxy)biphenyl-2,2'-diyl)bis(di-p-tolylphosphine) (to be referred to as "p-Tol-SEGPHOS" hereinafter), ((5,6),(5',6')-bis(methylenedioxy)biphenyl-2,2'-diyl)bis(di-3,5-xylylphosphine) (to be referred to as "DM-SEGPHOS" hereinafter), ((5,6),(5',6')-bis(methylenedioxy)biphenyl-2,2'-diyl)bis(di-4-methoxy-3,5-dimethylphenylphosphine) (to be referred to as "DMM-SEGPHOS" hereinafter), ((5,6),(5',6')-bis(methylenedioxy)biphenyl-2,2'-diyl)bis(di-4-methoxy-3,5-tert-butylphenylphosphine) (to be referred to as "DTBM-SEGPHOS" hereinafter), and ((5,6),(5',6')-bis(methylenedioxy)biphenyl-2,2'-diyl)bis(dicyclohexylphosphine) (to be referred to as "Cy-SEGPHOS" hereinafter).

In addition to the above, the following optically active phosphines can be cited.

2,2'-Dimethyl-6,6'-bis(diphenylphosphino)-1,1'-biphenyl (to be referred to as "BIPHEMP" hereinafter), 2,2'-dimethyl-6,6'-bis(di-p-tolylphosphino)-1,1'-biphenyl (to be referred to as "p-Tol-BIPHEMP" hereinafter), 2,2'-dimethyl-6,6'-bis(di-3,5-xylylphosphino)-1,1'-biphenyl (to be referred to as "DM-BIPHEMP" hereinafter), 2,2'-dimethyl-6,6'-bis(di-4-methoxy-3,5-dimethylphenylphosphino)-1,1'-biphenyl (to be referred to as "DMM-BIPHEMP" hereinafter), 2,2'-dimethyl-6,6'-bis(di-4-t-butoxy-3,5-dimethylphenylphosphino)-1,1'-biphenyl (to be referred to as "DTBM-BIPHEMP" hereinafter), 2,2'-dimethyl-6,6'-bis(dicyclohexylphosphino)-1,1'-biphenyl (to be referred to as "Cy-BIPHEMP" hereinafter), 2,2'-dimethoxy-6,6'-bis(diphenylphosphino)-1,1'-biphenyl (to be referred to as "MeO-BIPHEMP" hereinafter), 2,2'-dimethoxy-6,6'-bis(di-p-tolylphosphino)-1,1'-biphenyl (to be referred to as "p-Tol-MeO-BIPHEMP" hereinafter), 2,2'-dimethoxy-6,6'-bis(di-3,5-xylylphosphino)-1,1'-biphenyl (to be referred to as "DM-MeO-BIPHEMP" hereinafter), 2,2'-dimethoxy-6,6'-bis(di-4-methoxy-3,5-dimethylphenylphosphino)-1,1'-biphenyl (to be referred to as "DMM-MeO-BIPHEMP" hereinafter), 2,2'-dimethoxy-6,6'-bis(di-4-t-butoxy-3,5-dimethylphenylphosphino)-1,1'-biphenyl (to be referred to as "DTBM-MeO-BIPHEMP" hereinafter), 2,2'-dimethoxy-6,6'-bis(dicyclohexylphosphino)-1,1'-biphenyl (to be referred to as "Cy-MeO-BIPHEMP" hereinafter), 2,2'-dimethyl-3,3'-dichloro-4,4'-dimethyl-6,6'-bis(di-p-tolylphosphino)-1,1'-biphenyl (to be referred to as "p-Tol-CM-BIPHEMP" hereinafter), 2,2'-dimethyl-3,3'-dichloro-4,4'-dimethyl-6,6'-bis(di-3,5-xylylphosphino)-1,1'-biphenyl (to be referred to as "DM-CM-BIPHEMP" hereinafter), and 2,2'-dimethyl-3,3'-dichloro-4,4'-dimethyl-6,6'-bis(di-4-methoxy-3,5-dimethylphenylphosphino)-1,1'-biphenyl (to be referred to as "DMM-CM-BIPHEMP" hereinafter).

According to the invention, the 2-position olefin of piperitenone is hydrogenated with a complex consisting of the optically active phosphine represented by the general formula (2), (3) or (4) and a transition metal, and the desirable catalyst to be used in this hydrogenation is a transition metal complex consisting of an optically active phosphine containing a transition metal selected from rhodium, iridium and ruthenium and a transition metal. Most desirably, the hydrogenation is carried out by further adding an ammonium salt, a phosphonium salt or an alkali metal salt to such a complex consisting of an optically active phosphine and a transition metal.

Since each of these tertiary phosphines exists in (+)- and (−)-isomer forms, one of them is selected in response to the absolute configuration of pulegone of the intended optically active compound. That is, (S)-isomer is used for obtaining (1R) isomer, and (R)-isomer is used for obtaining (1S) isomer.

Rhodium Complex

As an illustrative example of the production method of a rhodium complex, it can be synthesized by allowing bis(cycloocta-1,5-diene)rhodium(I) tetrafluoroborate to react with an optically active bidentate phosphine (L) in accordance with the method described on pages 339 to 344 of $Jikken$-$Kagaku$-$Kouza$ 4th Edition, Vol. 18, Organic Metal Complex, 1991, edited by The Chemical Society of Japan, published by Maruzen. The following can be cited as illustrative examples of the rhodium complex.

$[Rh(cod)(L)]ClO_4$,
$[Rh(cod)(L)]PF_6$,
$[Rh(cod)(L)]BF_4$,
$[Rh(cod)(L)]BPh_4$,
$[Rh(cod)(L)]OTf$,
$[Rh(cod)(L)]OTs$,
$[Rh(cod)(L)]SbF_6$,
$[Rh(cod)(L)]OCOCF_3$,
$[Rh(cod)(L)]OCOC_2F_5$,
$[Rh(cod)(L)]OCOC_3F_7$,
$[Rh(nbd)(L)]ClO_4$,
$[Rh(nbd)(L)]PF_6$,
$[Rh(nbd)(L)]BF_4$,
$[Rh(nbd)(L)]BPh_4$,
$[Rh(nbd)(L)]OTf$,
$[Rh(nbd)(L)]OTs$,
$[Rh(nbd)(L)]SbF_6$,
$[Rh(nbd)(L)]OCOCF_3$,
$[Rh(nbd)(L)]OCOC_2F_5$,
$[Rh(nbd)(L)]OCOC_3F_7$,
$Rh(cod)(L)Cl$,
$Rh(nbd)(L)Cl$,
$Rh(cod)(L)Br$,
$Rh(nbd)(L)Br$,
$Rh(cod)(L)I$, and
$Rh(nbd)(L)I$.

Each of the abbreviations used in the above formulae indicates following respective compound.

L: Optically active phosphine represented by the general formula (2), (3) or (4),
OTf: trifluoromethanesulfonate,
OTs: p-toluenesulfonate,
Ph: phenyl,
cod: 1,5-cycooctadiene, and
nbd: norbornadiene.

Ruthenium Complex

Regarding the method for producing a ruthenium complex, it can be prepared by heating and stirring $[Ru(p$-$cymene)X_2]_2$ (X represents chlorine, bromine, and iodine) and L in methylene chloride and ethanol by the method described in a document (K. Mashima, K. Kusano, T. Ohta, R. Noyori and H. Takaya, $J.$ $Chem.$ $Soc.,$ $Chem.$ $Commn.,$ 1208 (1989)). The following can be cited as illustrative examples of the ruthenium complex.

$[RuCl(benzene)(L)]Cl$,
$[RuBr(benzene)(L)]Br$,
$[RuI(benzene)(L)]I$,
$[RuCl(p$-$cymene)(L)]Cl$,
$[RuBr(p$-$cymene)(L)]Br$,
$[RuI(p$-$cymene)(L)]I$,
$[RuCl(mesitylene)(L)]Cl$,
$[RuBr(mesitylene)(L)]Br$,
$[RuI(mesitylene)(L)]I$,
$[RuCl(hexamethylbenzene)(L)]Cl$,
$[RuBr(hexamethylbenzene)(L)]Br$,
$[RuI(hexamethylbenzene)(L)]I$,
$[\{RuCl(L)\}_2(\mu$-$Cl)_3][NH_2Me_2]$,
$[\{RuCl(L)\}_2(\mu$-$Cl)_3][NH_2Et_2]$,
$[\{RuCl(L)\}_2(\mu$-$Cl)_3][NH_2Pr_2]$, and
$[\{RuCl(L)\}_2(\mu$-$Cl)_3][NH_2i$-$Pr_2]$.

Iridium Complex

The iridium complex can be prepared by allowing L to react with $[Ir(cod)(CH_3CN)_2]BF_4$ while stirring in tetrahydrofuran in accordance with the method described in a document (K. Mashima, T. Akutagawa, X. Zhang, T. Taketomi, H. Kumobayashi and S. Akutagawa, *J. Organomet. Chem.*, 1992, 428, 213). The following can be cited as illustrative examples of the iridium complex.

[Ir(cod)(L)]ClO$_4$,
[Ir(cod)(L)]PF$_6$,
[Ir(cod)(L)]BF$_4$,
[Ir(cod)(L)]BPh$_4$,
[Ir(cod)(L)]OTf,
[Ir(cod)(L)]OTs,
[Ir(cod)(L)]SbF$_6$,
[Ir(cod)(L)]OCOCF$_3$,
[Ir(cod)(L)]OCOC$_2$F$_5$,
[Ir(cod)(L)]OCOC$_3$F$_7$,
[Ir(nbd)(L)]Cl)$_4$,
[Ir(nbd)(L)]PF$_6$,
[Ir(nbd)(L)]BF$_4$,
[Ir(nbd)(L)]BPh$_4$,
[Ir(nbd)(L)]OTf,
[Ir(nbd)(L)]OTs,
[Ir(nbd)(L)]SbF$_6$,
[Ir(nbd)(L)]OCOCF$_3$,
[Ir(nbd)(L)]OCOC$_2$F$_5$,
[Ir(nbd)(L)]OCOC$_3$F$_7$,
Ir(cod)(L)Cl,
Ir(nbd)(L)Cl,
Ir(cod)(L)Br,
Ir(nbd)(L)Br,
Ir(cod)(L)I, and
Ir(nbd) (L)I.

Since ethyl acetate (EtOAc) is excellent in both selectivity and optical yield as the solvent in the presence of a "complex consisting of an optically active phosphine and a transition-metal" selected from rhodium, iridium and ruthenium, a system in which the selectivity becomes high in the EtOAc solvent was established by a simple screening test. As the result, it was found that a quaternary ammonium salt or a quaternary phosphnium salt represented by a general formula (10)

$$R^5R^6R^7R^8AB \qquad (10)$$

(wherein each of $R^5$, $R^6$, $R^7$ and $R^8$ means an alkyl group having from 1 to 16 carbon atoms, phenyl group or benzyl group, A means nitrogen atom or phosphorus atom, and B means a halogen atom such as chlorine, bromine or iodine, a carboxylate or a sulfonate) is useful, and its illustrative examples include quaternary ammonium salts such as Me$_4$NCl, Me$_4$NBr, Me$_4$NI, Et$_4$NCl, Et$_4$NBr, Et$_4$NI, Bu$_4$NCl, Bu$_4$NBr, Bu$_4$NI, (Benzyl)Me$_3$NCl, (Benzyl)Me$_3$NBr, (Benzyl)Me$_3$NI, (Benzyl)Et$_3$NCl, (Benzyl)Et$_3$NBr, (Benzyl)Et$_3$NI, (C$_8$H$_{17}$)Me$_3$NCl, (C$_8$H$_{17}$)Me$_3$NBr, (C$_8$H$_{17}$)Me$_3$NI, (C$_{16}$H$_{33}$)Me$_3$NCl, (C$_{16}$H$_{33}$)Me$_3$NBr, (C$_{16}$H$_{33}$)Me$_3$NI, Me$_4$NOTf, Me$_4$NOTs, Me$_4$NOAc, Me$_4$NOCOCF$_3$, n-Bu$_4$NOTf, n-Bu$_4$NOTs, n-Bu$_4$NOAc and n-Bu$_4$NOCOCF$_3$, and quaternary phosphonium salts such as MePh$_3$PCl, MePh$_3$PBr, MePh$_3$PI, EtPh$_3$PCl, EtPh$_3$PBr, EtPh$_3$PI, BuPh$_3$PCl, BuPh$_3$PBr, BuPh$_3$PI, Ph$_4$PCl, Ph$_4$PBr, Ph$_4$PI, (C$_6$H$_{13}$)Ph$_3$PCl, (C$_6$H$_{13}$)Ph$_3$PBr, (C$_6$H$_{13}$)Ph$_3$PI, (C$_7$H$_{15}$)Ph$_3$PCl, (C$_7$H$_{15}$)Ph$_3$PBr, (C$_7$H$_{15}$)Ph$_3$PI, (C$_8$H$_{17}$) Ph$_3$PCl, (C$_8$H$_{17}$)Ph$_3$PBr, (C$_8$H$_{17}$)Ph$_3$PI, (C$_{16}$H$_{33}$)Ph$_3$PCl, (C$_{16}$H$_{33}$)Ph$_3$PBr, (C$_{16}$H$_{33}$)Ph$_3$PI, (C$_{16}$H$_{33}$)Bu$_3$PCl, (C$_{16}$H$_{33}$)Bu$_3$PBr, (C$_{16}$H$_{33}$)Bu$_3$PI, ClPPh$_3$CH$_2$PPh$_3$Cl, ClPPh$_3$(CH$_2$)$_2$PPh$_3$Cl, ClPPh$_3$(CH$_2$)$_3$PPh$_3$Cl, ClPPh$_3$(CH$_2$)$_4$PPh$_3$Cl, ClPPh$_3$(CH$_2$)$_5$PPh$_3$Cl, ClPPh$_3$(CH$_2$)$_6$PPh$_3$Cl, BrPPh$_3$CH$_2$PPh$_3$Br, BrPPh$_3$(CH$_2$)$_2$Ph$_3$Br, BrPPh$_3$(CH$_2$)$_3$Ph$_3$Br, BrPPh$_3$(CH$_2$)$_4$Ph$_3$Br, BrPPh$_3$(CH$_2$)$_5$Ph$_3$Br, BrPPh$_3$(CH$_2$)$_6$Ph$_3$Br, IPPh$_3$CH$_2$PPh$_3$I, IPPh$_3$(CH$_2$)$_2$PPh$_3$I, IPPh$_3$(CH$_2$)$_3$PPh$_3$I, IPPh$_3$(CH$_2$)$_4$PPh$_3$I, IPPh$_3$(CH$_2$)$_5$PPh$_3$I and IPPh$_3$(CH$_2$)$_6$PPh$_3$I.

Also useful is a salt represented by a general formula (11):

$$MZ \qquad (11)$$

(wherein M means a metal of Li, Na or K, and Z means a halogen atom such as Cl, Br or I), and its illustrative examples include metal salts such as LiCl, LiBr, LiI, NaCl, NaBr, NaI, KCl, KBr and KI.

Ammonium salts such as (Bn)Et$_3$NCl, (Bn)Et$_3$NBr and (Bn)Et$_3$NI and phosphonium salts such as such as BuPh$_3$PCl, BuPh$_3$PBr, BuPh$_3$PI, (C$_6$H$_{13}$)Ph$_3$Br and BrPPh$_3$ (CH$_2$)$_4$PPh$_3$Br can be selected, from which high selectivity is obtained (in which Bn is benzyl group, Et is ethyl group, Ph is phenyl group, and Bu is butyl group).

Regarding the ligand, DM-BINAP can be selected from BINAPs, DM-H$_8$-BINAP can be selected from H$_8$-BINAPs and DTBM-SEGPHOS can be selected from SEGPHOS, from which high selectivity is obtained.

This reaction is carried out under a hydrogen pressure of about from 5 to 100 Kg/cm$^2$ (0.5 to 10 Mpa), at a reaction temperature of about from 10 to 100° C. and for a reaction time of about from 5 to 20 hours. Also, amount of the transition metal—optically active phosphine complex to be used is about from 1/5,000 to 1/50,000 mole based on piperitenone. Amount of the additive (an ammonium salt, a phosphonium salt or an alkali metal) to be used is about from 0.2 to 2.0 equivalent based on the transition metal—optically active phosphine complex.

Preferred among the solvents are without solvent, or in a solvent such as THF, acetone and ethyl acetate.

According to the invention, pulegol represented by the formula (6) is obtained by, as the second hydrogenation reaction, hydrogenating pulegone represented by the formula (5) with a ruthenium-phosphine-amine complex. The reaction formula is shown below.

As the second hydrogenation reaction method, a system of a ruthenium complex-amine-base is most excellent in hydrogenating the obtained pulegone (5), and a result of examination revealed that an achiral ligand can be used as the ruthenium complex. Examples of the ruthenium complex having such a ligand are shown below. In the following examples, Et means ethyl group, dmf means dimethylformamide and n is from 1 to 5.

Ru$_2$Cl$_4$((S)-binap)$_2$(NEt$_3$),
Ru$_2$Cl$_4$((S)-tol-binap)$_2$(NEt$_3$),
Ru$_2$Cl$_4$((S)-dm-binap)$_2$(NEt$_3$),
RuCl$_2$((S)-binap)(dmf)$_n$,
RuCl$_2$((S)-tol-binap)(dmf)$_n$,
RuCl$_2$((S)-dmbinap)(dmf)$_n$,
RuCl$_2$(PPh$_3$)$_3$,
RuCl$_2$[(p-tolyl)$_3$P]$_3$,
RuCl$_2$[(o-tolyl)$_3$P]$_3$,
RuCl$_2$(bpbp), RuCl$_2$(1,2-diphos)$_2$,
RuCl$_2$(1,3-diphos)$_2$,
RuCl$_2$(1,4-diphos)$_2$,
RuCl$_2$(1,5-diphos)$_2$,
RuCl$_2$(1,6-diphos)$_2$ Further, each abbreviation in the above formulae indicates the following respective compound.
bpbp: 2,2'-bis(diphenylphosphino)-1,1'-biphenyl,
1,2-diphos: 1,2-bis(diphenylphosphino)ethane,
1,3-diphos: 1,3-bis(diphenylphosphino)propane,
1,4-diphos: 1,4-bis(diphenylphosphino)butane,
1,5-diphos: 1,5-bis(diphenylphosphino)pentane,
1,6-diphos: 1,6-bis(diphenylphosphino)hexane The amine compounds include a primary amine compound, a secondary amine compound, and a diamine compound. The following amine compounds are typical example: primary amine compounds such as methylamine, ethylamine, propylamine, butylamine, penthylamine, hexylamine, cyclopenthylamine, cyclohexylamine and benzylamine; secondary amine compounds such as dimethylamine, diethylamine, dipropylamine, dibutylamine, dipenthylamine, dihexylamine, dicyclopenthylamine, dicyclohexylamine, dibenzylamine, diphenylamine, phenylethylamine, piperidine and piperadine; and diamine compounds such as methylenediamine, 1,2-ethylenediamine, 1,2-propanediamine, 1,3-propanediamine, 1,4-butanediamine, 2,3-butanediamine, 1,2-cyclopentanediamine, 1,2-cyclohexanediamien, N-methylethylenediamine, N,N'-dimethylethylenediamine, N,N,N'-trimethylethylenediamine, N,N,N',N'-tetramethylethylenediamine, o-phenylenediamine, p-phenylenediamine and 1,2-diphenylethylenediamine.

As the amine, 1,2-ethylenediamine, 1,3-propanediamine, 1,4-butanediamine and 1,2-diphenylethylenediamine are preferably selected, of which 1,2-ethylenediamine and 1,3-propanediamine are most superior.

As the base, metal salts each represented by the following formula (12)

$$M'Y \qquad (12)$$

wherein M' represents an alkali metal or alkaline earth metal and Y represents a hydroxy, alkoxy, mercapto, naphthyl group or carbonate, or quaternary ammonium salts can be employed. Specific examples include LiOH, LiOMe, LiOEt, LiOi-Pr, LiOt-Bu, NaOH, NaOMe, NaOEt, NaOi-Pr, NaOt-Bu, KOH, KOMe, KOEt, KOi-Pr, KOt-Bu, KC$_{10}$H$_8$, Li$_2$CO$_3$, K$_2$CO$_3$ and Na$_2$CO$_3$. Quaternary ammonium salts are also usable.

As the base, pottassium hydroxide (KOH) and potassium t-butoxide (KOt-Bu) are preferably selected.

Amount of the catalyst is about from 1/1,000 to 1/30,000 mole based on the substitute pulegone. Amount of the amine is about from 1 to 2 equivalent based on the catalyst. Amount of the base is about from 0.5 to 100 equivalent, or preferably about from 10 to 50 equivalent, based on the catalyst.

In the invention, any liquid solvent is usable insofar as it can solubilize reaction raw materials (pulegone) and catalyst system. Examples include aromatic hydrocarbon solvents such as toluene and xylene, aliphatic hydrocarbon solvents such as pentane and hexane, halogen-containing hydrocarbon solvents such as methylene chloride, ether solvents such as ether and tetrahydrofuran, alcohol solvents such as methanol, ethanol, isopropanol, butanol, and benzylalcohol, and hetro-atom-containing organic solvents such as acetonitrile, DMF and DMSO. The target product is an alcohol so that alcohol solvents are most suited, with isopropanol being more preferred.

The amount of the solvent is judged from the solubility of the reaction substrate and economy. When isopropanol is employed, reaction can be effected at a low concentration of 1% or less or in a nearly solventless manner, though depending on the kind of the substrate. Preferred is 0.1 to 2.0 by volume. The hydrogen pressure within a range of 1 to 100 Kg/cm$^2$ (0.1 to 10 MPa) is desired, with 5 to 50 Kg/cm$^2$ (0.5 to 5 MPa) being more preferred.

Although the reaction is preferably conducted within a range of 0 to 150° C., with 10 to 50° C. being more preferred. The reaction time differs with the concentration of the reaction substrate or reaction condition such as temperature and pressure, but reaction is completed within several minutes to 30 hours.

It is desirable that the thus formed pulegol is subjected to the subsequent reaction after increasing its chemical purity and optical purity by recrystallization. High purity pulegol can be obtained by recrystallizing it using a hydrocarbon solvent such as hexane, cyclohexane, heptane, pentane, octane or isooctane. Amount of the hydrocarbon solvent to be used is from 0.5 to 10 times, preferably from 1 to 3 times, based on pulegol. The temperature at the time of crystallization is selected within the range of from −70° C. to 0° C., and generally carried out within the range of from −40° C. to 0° C.

According to the invention, 1-menthol represented by the formula (7) is obtained by, as the third hydrogenation reaction, hydrogenating pulegol represented by the formula (6) with a transition metal catalyst. The reaction formula is shown below.

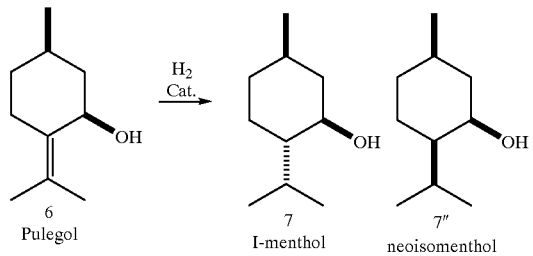

6
Pulegol

7
I-menthol

7″
neoisomenthol

As the third hydrogenation, the thus obtained pulegol (6) is hydrogenated with a generally and frequently used heterogeous hydrogen catalyst. Examples include Raney nickel, platinum oxide, platinum black, palladium black, rhodium black, palladium-carbon, iridium-carbon, rhodium-carbon, ruthenium-carbon, osmium-carbon, palladium-alumina, palladium-silica and palladium-silica-alumina. Specific examples include Raney nickel, palladium-carbon, iridium-carbon, rhodium-carbon, ruthenium-carbon, palladium-alumina, palladium-silica and palladium-silica-alumina, and most specific examples includes palladium-carbon and palladium-silica-alumina.

This reaction is carried out under a hydrogen pressure of about from 5 to 50 Kg/cm$^2$ (0.5 to 5 MPa), at a reaction temperature of about from 20 to 100° C. and for a reaction time of about from 5 to 20 hours. Also, mount of the catalyst to be used is about from 0.01 to 1.0 wt. % based on pulegol.

Preferred among the solvents are without solvent, or in a solvent such as THF, acetone and ethyl acetate.

Also, a homogeneous catalyst in the form of a ruthenium-phosphine-dicarboxylate complex is used in the third hydrogenation of the thus obtained pulegol (6).

As the ligand to be used in the catalyst for hydrogenating the olefin of pulegol, there is an optically active phosphine represented by a general formula (2)

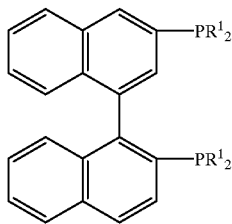

(2)

wherein R¹ represents an aryl group which may have a substituent group or a cycloalkyl group having from 3 to 8 carbon atoms.

In this general formula (2) of the present invention, R¹ is a phenyl group which may have a substitutent group, a naphthyl group which may have substitutent group or a cycloalkyl group having from 3 to 8 carbon atoms.

Examples of the substituents thereof include lower alkyl groups having 1 to 4 carbon atoms, such as methyl, ethyl, propyl, isopropyl, n-butyl, t-butyl, and isobutyl; halogen atoms such as fluorine, chlorine, and bromine; lower alkoxy groups having 1 to 4 carbon atoms, such as methoxy, ethoxy, propoxy, and butoxy; halogenated lower alkyl groups such as trifluoromethyl and trichloromethyl, and benzyloxy.

Preferred examples of R¹ include phenyl, 4-tolyl, 3-tolyl, 4-methoxyphenyl, 3,5-xylyl, 3,5-di-tert-butylphenyl, 4-methoxy-3,5-dimethylphenyl, 4-methoxy-3,5-di-tert-butylphenyl, naphthyl, cyclohexyl and cyclopentyl.

Examples of the optically active phosphine to be desirably used according to this general formula (2) include tertiary phosphines described in JP-A-61-63690 and JP-A-62-265293 (the term "JP-A" as used herein means an "unexamined published Japanese patent application"), and the following can be cited as illustrative examples. 2,2'-Bis(diphenylphosphino)-1,1'-binaphthyl (to be referred to as "BINAP" hereinafter), 2,2'-bis[di(p-tolyl)phosphino]-1,1'-binaphthyl (to be referred to as "Tol-BINAP" hereinafter), 2,2'-bis[di(3,5-xylyl)phosphino]-1,1'-binaphthyl (to be referred to as "DM-BINAP" hereinafter), 2,2'-bis[di(3,5-di-tert-butylphenyl)phosphino]-1,1'-binaphthyl (to be referred to as "(t-Bu)₂-BINAP" hereinafter), 2,2'-bis[di(4-methoxy-3,5-dimethylphenyl)phosphino]-1,1'-binaphthyl (to be referred to as "DMM-BINAP" hereinafter), 2,2'-bis(dicyclohexylphosphino)-1,1'-binaphthyl (to be referred to as "Cy-BINAP" hereinafter), and 2,2'-bis(dicyclopentylphosphino)-1,1'-binaphthyl (to be referred to as "Cp-BINAP" hereinafter).

Also, among optically active phosphines represented by a general formula (3)

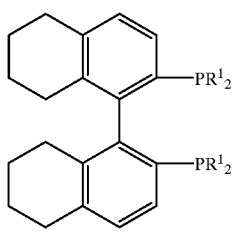

(3)

wherein R¹ represents an aryl group which may have a substituent group or a cycloalkyl group having from 3 to 8 carbon atoms.

In this general formula (3) of the present invention, R¹ is a phenyl group which may have a substitutent group, a naphthyl group which may have substitutent group or a cycloalkyl group having from 3 to 8 carbon atoms.

Examples of the substituents thereof include lower alkyl groups having 1 to 4 carbon atoms, such as methyl, ethyl, propyl, isopropyl, n-butyl, t-butyl, and isobutyl; halogen atoms such as fluorine, chlorine, and bromine; lower alkoxy groups having 1 to 4 carbon atoms, such as methoxy, ethoxy, propoxy, and butoxy; halogenated lower alkyl groups such as trifluoromethyl and trichloromethyl, and benzyloxy.

Preferred examples of R¹ include phenyl, 4-tolyl, 3-tolyl, 4-methoxyphenyl, 3,5-xylyl, 3,5-di-tert-butylphenyl, 4-methoxy-3,5-dimethylphenyl, 4-methoxy-3,5-di-tert-butylphenyl, naphthyl, cyclohexyl and cyclopentyl.

Examples of the optically active phosphine to be desirably used according to this general formula (3) include tertiary phosphines described in JP-A-4-139140 (the term "JP-A" as used herein means an "unexamined published Japanese patent application"), and the following can be cited as illustrative examples. 2,2'-Bis{diphenylphosphino}-5,5'6,6',7,7',8,8'-octahydrobinaphthyl (to be referred to as "H₈-BINAP" hereinafter), 2,2'-bis{di(p-tolyl)phosphino}-5,5'6,6',7,7',8,8'-octahydrobinaphthyl (to be referred to as "p-Tol-H₈-BINAP" hereinafter), 2,2'-bis{di-(3,5-xylyl)phosphino}-5,5'6,6',7,7',8,8'-octahydrobinaphthyl (to be referred to as "DM-H₈-BINAP" hereinafter), and 2,2'-bis{di-(4-methoxy-3,5-dimethylphenyl)phosphino}-5,5'6,6',7,7',8,8'-octahydrobinaphthyl (to be referred to as "DMM-H₈-BINAP" hereinafter).

Also, among optically active phosphines represented by a general formula (4)

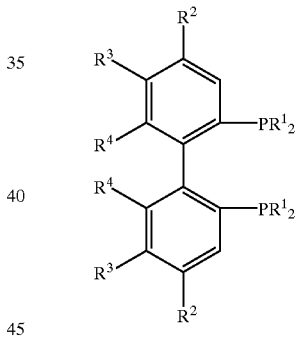

(4)

wherein R¹ represents an aryl group which may have a substituent group or a cycloalkyl group having from 3 to 8 carbon atoms, R² represents hydrogen atom or a lower alkyl group having from 1 to 4 carbon atoms, R³ represents hydrogen atom methyl group, methoxy group or a halogen atom, and R⁴ represents methyl group or methoxy group, or R³ and R⁴ may be coupled together to form methylenedioxy group.

In this general formula (4) of the present invention, R¹ is a phenyl group which may have a substitutent group, a naphthyl group which may have substitutent group or a cycloalkyl group having from 3 to 8 carbon atoms.

Examples of the substituents thereof include lower alkyl groups having 1 to 4 carbon atoms, such as methyl, ethyl, propyl, isopropyl, n-butyl, t-butyl, and isobutyl; halogen atoms such as fluorine, chlorine, and bromine; lower alkoxy groups having 1 to 4 carbon atoms, such as methoxy, ethoxy, propoxy, and butoxy; halogenated lower alkyl groups such as trifluoromethyl and trichloromethyl, and benzyloxy.

Preferred examples of R¹ include phenyl, 4-tolyl, 3-tolyl, 4-methoxyphenyl, 3,5-xylyl, 3,5-di-tert-butylphenyl, 4-methoxy-3,5-dimethylphenyl, 4-methoxy-3,5-di-tert-butylphenyl, naphthyl, cyclohexyl and cyclopentyl.

Examples of the optically active phosphine to be desirably used according to this general formula (4) include tertiary phosphines described in JP-A-11-269,185 (the term "JP-A" as used herein means an "unexamined published Japanese patent application"), and the following can be cited as illustrative examples.

((5,6), (5',6')-Bis(methylenedioxy)biphenyl-2,2'-diyl)bis(diphenylphosphine) (to be referred to as "SEGPHOS" hereinafter), ((5,6),(5',6')-bis(methylenedioxy)biphenyl-2,2'-diyl)bis(di(p-tolyl)phosphine) (to be referred to as "p-Tol-SEGPHOS" hereinafter), ((5,6),(5',6')-bis(methylenedioxy)biphenyl-2,2'-diyl)bis(di(3,5xylyl)phosphine) (to be referred to as "DM-SEGPHOS" hereinafter), ((5,6),(5',6')-bis(methylenedioxy)biphenyl-2,2'-diyl)bis(di(4-methoxy-3,5-dimethylphenyl)phosphine) (to be referred to as "DMM-SEGPHOS" hereinafter), ((5,6),(5',6')-bis(methylenedioxy)biphenyl-2,2'-diyl)bis(di(4-methoxy-3,5-tert-butylphenyl)phosphine) (to be referred to as "DTBM-SEGPHOS" hereinafter), and ((5,6),(5',6')-bis(methylenedioxy)biphenyl-2,2'-diyl)bis(di(cyclohexyl)phosphine) (to be referred to as "Cy-SEGPHOS" hereinafter). Also included are 2,2'-dimethyl-6,6'-bis(diphenylphosphino)-1,1'-biphenyl (to be referred to as "BIPHEMP" hereinafter), 2,2'-dimethyl-6,6'-bis(di(p-tolyl)phosphino)-1,1'-biphenyl (to be referred to as "p-Tol-BIPHEMP" hereinafter), 2,2'-dimethyl-6,6'-bis(di(3,5-xylyl)phosphino)-1,1'-biphenyl (to be referred to as "DM-BIPHEMP" hereinafter), 2,2'-dimethyl-6,6'-bis(di(4-methoxy-3,5-dimethylphenyl)phosphino)-1,1'-biphenyl (to be referred to as "DMM-BIPHEMP" hereinafter), 2,2'-dimethyl-6,6'-bis(di(4-t-butoxy-3,5-dimethylphenyl)phosphino)-1,1'-biphenyl (to be referred to as "DTBM-BIPHEMP" hereinafter), 2,2'-dimethyl-6,6'-bis(di(cyclohexyl)phosphino)-1,1'-biphenyl (to be referred to as "Cy-BIPHEMP" hereinafter), 2,2'-dimethoxy-6,6'-bis(diphenylphosphino)-1,1'-biphenyl (to be referred to as "MeO-BIPHEP" hereinafter), 2,2'-dimethoxy-6,6'-bis(di(p-tolyl)phosphino)-1,1'-biphenyl (to be referred to as "p-Tol-MeO-BIPHEP" hereinafter), 2,2'-dimethoxy-6,6'-bis(di(3,5-xylyl)phosphino)-1,1'-biphenyl (to be referred to as "DM-MeO-BIPHEP" hereinafter), 2,2'-dimethoxy-6,6'-bis(di(4-methoxy-3,5-dimethylphenyl)phosphino)-1,1'-biphenyl (to be referred to as "DMM-MeO-BIPHEP" hereinafter), 2,2'-dimethoxy-6,6'-bis(di(4-t-butoxy-3,5-dimethylphenyl)phosphino)-1,1'-biphenyl (to be referred to as "DTBM-MeO-BIPHEP" hereinafter), 2,2'-dimethoxy-6,6'-bis(di(cyclohexyl)phosphino)-1,1'-biphenyl (to be referred to as "Cy-MeO-BIPHEP" hereinafter), 2,2'-dimethyl-3,3'-dichloro-4,4'-dimethyl-6,6'-bis(di(p-tolyl)phosphino)-1,1'-biphenyl (to be referred to as "p-Tol-CM-BIPHEMP" hereinafter), 2,2'-dimethyl-3,3'-dichloro-4,4'-dimethyl-6,6'-bis(di(3,5-xylyl)phosphino)-1,1'-biphenyl (to be referred to as "DM-CM-BIPHEMP" hereinafter), and 2,2'-dimethyl-3,3'-dichloro-4,4'-dimethyl-6,6'-bis(di(4-methoxy-3,5-dimethylphenyl)phosphino)-1,1'-biphenyl (to be referred to as "DMM-CM-BIPHEMP" hereinafter).

Also, as still another ligand to be used in the catalyst for the third hydrogenation reaction, there is a phosphine represented by a general formula (8)

$$R^1{}_2P-(CH_2)_n-PR^1{}_2 \quad (8)$$

wherein $R^1$ represents an aryl group which may have a substituent group or a cycloalkyl group having from 3 to 8 carbon atoms, and n is an integer of from 1 to 7.

In this general formula (8) of the present invention, $R^1$ is a phenyl group which may have a substituent group, a naphthyl group which may have substitutent group or a cycloalkyl group having from 3 to 8 carbon atoms.

Examples of the substituents thereof include lower alkyl groups having 1 to 4 carbon atoms, such as methyl, ethyl, propyl, isopropyl, n-butyl, t-butyl, and isobutyl; halogen atoms such as fluorine, chlorine, and bromine; lower alkoxy groups having 1 to 4 carbon atoms, such as methoxy, ethoxy, propoxy, and butoxy; halogenated lower alkyl groups such as trifluoromethyl and trichloromethyl, and benzyloxy.

Preferred examples of $R^1$ include phenyl, 4-tolyl, 3-tolyl, 4-methoxyphenyl, 3,5-xylyl, 3,5-di-tert-butylphenyl, 4-methoxy-3,5-dimethylphenyl, 4-methoxy-3,5-di-tert-butylphenyl, naphthyl, cyclohexyl and cyclopentyl. The following can be exemplified as suitably useful phosphines of the general formula (8).

Bis(diphenylphosphino)methane, 1,2-bis(diphenylphosphino)ethane, 1,3-bis(diphenylphosphino)propane, 1,4-bis(diphenylphosphino)butane, 1,5-bis(diphenylphosphino)pentane, 1,6-bis(diphenylphosphino)hexane, 1,7-bis(diphenylphosphino)heptane, bis(di(p-tolyl)phosphino)methane, 1,2-bis(di(p-tolyl)phosphino)ethane, 1,3-bis(di(p-tolyl)phosphino)propane, 1,4-bis(di(p-tolyl)phosphino)butane, 1,5-bis(di(p-tolyl)phosphino)pentane, 1,6-bis(di-p-tolyl)phosphino)hexane, 1,7-bis(di(p-tolyl)phosphino)heptane, bis(di(3,5-xylyl)phosphino)methane, 1,2-bis(di(3,5-xylyl)phosphino)ethane, 1,3-bis(di(3,5-xylyl)phosphino)propane, 1,4-bis(di(3,5-xylyl)phosphino)butane, 1,5-bis(di(3,5-xylyl)phosphino)pentane, 1,6-bis(di(3,5-xylyl)phosphino)hexane, 1,7-bis(di(3,5-xylyl)phosphino)heptane, bis(di(4-methoxy-3,5-di-tert-butylphenyl)phosphino)methane, 1,2-bis(di(4-methoxy-3,5-di-tert-butylphenyl)phosphino) ethane, 1,3-bis(di(4-methoxy-3,5-di-tert-butylphenyl)phosphino)propane, 1,4-bis(di(4-methoxy-3,5-di-tert-butylphenyl)phosphino)butane, 1,5-bis(di(4-methoxy-3,5-di-tert-butylphenyl)phosphino)pentane, 1,6-bis(di(4-methoxy-3,5-di-tert-butylphenyl)phosphino)hexane, 1,7-bis(di(4-methoxy-3,5-di-tert-butylphenyl)phosphino)heptane, bis(di(3,5-difluorophenyl)phosphino)methane, 1,2-bis(di(3,5-difluorophenyl)phosphino)ethane, 1,3-bis(di(3,5-difluorophenyl)phosphino)propane, 1,4-bis(di(3,5-difluorophenyl)phosphino)butane, 1,5-bis(di(3,5-difluorophenyl)phosphino)pentane, 1,6-bis(di(3,5-difluorophenyl)phosphino)hexane, 1,7-bis(di(3,5-difluorophenyl)phosphino)heptane, bis(di(3,5-ditrifluoromethylphenyl)phosphino)methane, 1,2-bis(di(3,5-ditrifluoromethylphenyl)phosphino)ethane, 1,3-bis(di(3,5-ditrifluoromethylphenyl)phosphino)propane, 1,4-bis(di(3,5-ditrifluoromethylphenyl)phosphino)butane, 1,5-bis(di(3,5-ditrifluoromethylphenyl)phosphino)pentane, 1,6-bis(di(3,5-ditrifluoromethylphenyl)phosphino)hexane and 1,7-bis(di(3,5-ditrifluoromethylphenyl)phosphino)heptane.

In addition to the above, there is a phosphine represented by a general formula (9)

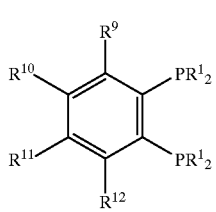

(9)

wherein $R^1$ represents an aryl group which may have a substituent group or a cycloalkyl group having from 3 to 8 carbon atoms, each of $R^7$ to $R^{10}$ represents hydrogen atom, methyl group, methoxy group, phenyl group, a halogen atm or trifluoromethyl group, or $R^7$ and $R^8$, $R^8$ and $R^9$ or $R^9$ and $R^{10}$ together form methylenedioxy group or $R^8$ and $R^9$ together from a cycloalkyl ring.

In this general formula (9) of the present invention, $R^1$ is a phenyl group which may have a substitutent group, a naphthyl group which may have substitutent group or a cycloalkyl group having from 3 to 8 carbon atoms.

Examples of the substituents thereof include lower alkyl groups having 1 to 4 carbon atoms, such as methyl, ethyl, propyl, isopropyl, n-butyl, t-butyl, and isobutyl; halogen atoms such as fluorine, chlorine, and bromine; lower alkoxy groups having 1 to 4 carbon atoms, such as methoxy, ethoxy, propoxy, and butoxy; halogenated lower alkyl groups such as trifluoromethyl and trichloromethyl, and benzyloxy.

Preferred examples of $R^1$ include phenyl, 4-tolyl, 3-tolyl, 4-methoxyphenyl, 3,5-xylyl, 3,5-di-tert-butylphenyl, 4-methoxy-3,5-dimethylphenyl, 4-methoxy-3,5-di-tert-butylphenyl, naphthyl, cyclohexyl and cyclopentyl.

The following can be exemplified as suitably useful phosphines of the general formula (9). 1,2-Bis (diphenylphosphino)benzene, 1,2-bis(di(p-tolyl)phosphino) benzene, 1,2-bis(di(3,5-xylyl)phosphino)benzene, 1,2-bis(di (4-methoxy-3,5-di-tert-butylphenyl)phosphino)benzene, 1,2-bis(di(3,5-difluoropheyl)phosphino)benzene, 1,2-bis(di (3,5-di-trifluoromethylphenyl)phosphino)benzene, 1,2-bis (diphenylphosphino)-4,5-methylenedioxybenzene, 1,2-bis (di(p-tolyl)phosphino)-4,5-methylenedioxybenzene, 1,2-bis (di(3,5-xylyl)phosphino)-4,5-methylenedioxybenzene, 1,2-bis(di(4-methoxy-3,5-di-tert-butylphenyl)phosphino)-4,5-methylenedioxybenzene, 1,2-bis(di(3,5-difluorophenyl) phosphino)-4,5-methylenedioxybenzene, 1,2 -bis(di(3,5-ditrifluoromethylphenyl)phosphino)-4,5-methylenedioxybenzene, 2,3-bis(diphenylphosphino) naphthalene, 2,3-bis(di(p-tolyl)phosphino)naphthalene, 2,3-bis(di(3,5-xylyl)phosphino)naphthalene, 2,3-bis(di(4-methoxy-3,5-di-tert-butylphenyl)phosphino)naphthalene, 2,3-bis(di(3,5-difluorophenyl)phosphino)naphthalene, 2,3-bis(di(3,5-ditrifluorophenyl)phosphino)naphthalene, 2,3-bis (diphenylphosphino)-5,6,7,8-octahydronaphthalene, 2,3-bis (di(p-tolyl)phosphino)-5,6,7,8-octahydronaphthalene, 2,3-bis(di(3,5-xylyl)phosphino)-5,6,7,8-octahydronaphthalene, 2,3-bis(di(4-methoxy-3,5-di-tert-butylphenyl)phosphino)-5, 6,7,8-octahydronaphthalene, 2,3-bis(di(3,5-difluorophenyl) phosphino)-5,6,7,8-octahydronaphthalene and 2,3-bis(di(3, 5-di-trifluoromethylphenyl)phosphino)-5,6,7,8-octahydronaphthalene.

Ruthenium Dicarboxylate Complex

As an illustrative example of the method for the production of ruthenium complexes, they can be synthesized in accordance with the method described by Ohta et al. in *Inorg. Chem.*, vol. 27, p. 566, 1998. The following can be cited as illustrative examples of the dicarboxylate complex.
Ru(OAc)$_2$(L)
Ru (OCOPh)$_2$ (L)
Ru(OCOC$_2$H$_5$)$_2$(L)
Ru(OCOC$_3$H$_7$)$_2$(L)
Ri(OCO-i-C$_3$H$_7$)$_2$(L)
Ru(OCOC$_4$H$_9$)$_2$(L)
Ru(OCO-t-C$_4$H$_9$)$_2$(L)
Ru(OCOCH$_2$OCO)(L)
Ru(OCOC$_2$H$_4$OCO)(L)
Ru(OCOC$_3$H$_6$OCO)(L)
Ru(OCOC$_4$H$_8$OCO)(L)

Abbreviations in the above formulae indicate the following compounds.
L: an optically active phosphine represented by the general formula (2), (3), (4), (8) or (9)

Ac: acetyl
Ph: phenyl

As the third hydrogenation, the most high selectivity was obtained when the pulegol (6) was hydrogenated using a ruthenium dicarboxylate complex. Though other reaction conditions are not different from those of general hydrogenation, the reaction is carried out at a reaction temperature of from 20 to 100° C. for a reaction period of from 5 to 20 hours under an hydrogen pressure of from 5 to 50 kg/cm$^2$ (0.5 to 5 MPa), without solvent or in a solvent such as toluene, ethyl acetate, methanol, ethanol, 2-propanol, methylene chloride or tetrahydrofuran.

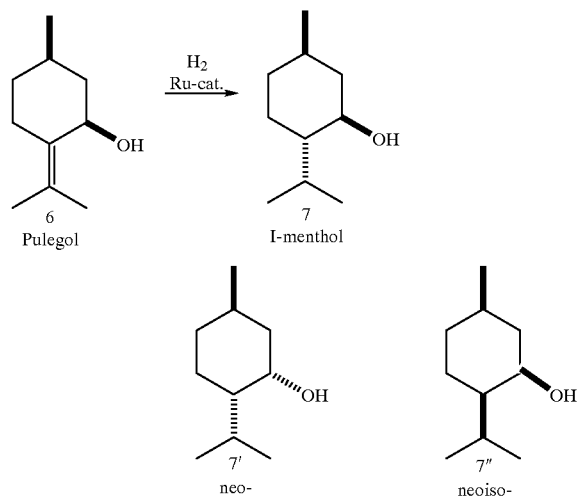

6 Pulegol
7 l-menthol
7' neo-
7" neoiso-

By the method found by the invention in which piperitenone is hydrogenated by an optically active phosphine ligand and a transition metal complex, it become possible to produce pulegone with high position selectivity and also with high optical yield. In addition, 1-menthol can be produced by carrying out selective hydrogenation of pulegone with a ruthenium-phosphine-amine complex in the presence of base to obtain pukegol and then hydrogenation it with a transition metal catalyst. That is, there provided a method for producing 1-menthol by an inexpensive method with high yield, by repeating hydrogenation reaction there times.

The invention is illustratively described in the following with reference to inventive and comparative examples, though the invention is not restricted by these examples.

In this connection, the following instruments were used for the measurement of physical properties of the compounds obtained in the inventive and comparative examples.
NMR DRX500 (mfd. by Bruker)
$^1$H-NMR (500 MHz; internal standard: tetramethylsilane)
$^{31}$P-NMR (202 MHz; internal standard: 85% phosphoric acid)
GLC 5890-II (mfd. by Hewlett Packard)
GC-Column Conversion ratio: FFAP 30 m×0.53 mm (GL Science Ltd.)
Optical yield: Chiraldex B-TA 30 m×0.25 mm (ASTEC)

SYNTHESIS EXAMPLE 1

Synthesis of Piperitenone Using 4-hydroxy-2-butanone

A 688 ml (6.0 mol) portion of mesityl oxide was put into a one liter capacity four neck flask, 4.18 ml (10 mmol) of 40% benzyltrimethylammonium hydroxide aqueous solution was added dropwise thereto and the mixture was heated to 80° C. To this was added dropwise 172 ml (2.0 mol) of 4-hydroxy-2-butanone spending 1 hour while keeping at 80° C. After completion of the dropwise addition, this was stirred for 30 minutes and then neutralized by adding dropwise 0.69 ml of acetic acid. By carrying out distillation of the reaction solution under a reduced pressure, 180 g of piperitenone was obtained. Yield 60%.

Synthesis Example 2

Synthesis of Piperitenone Using 4-hydroxy-2-butanone

A 688 ml (6.0 mol) portion of mesityl oxide was put into a one liter capacity four neck flask and mixed with 6.30 g (0.02 mol) of barium hydroxide octahydrate and 2.28 g (10 mmol) of benzyltriethylammonium chloride, and the mixture was heated to 80° C. To this was added dropwise 172 ml (2.0 mol) of 4-hydroxy-2-butanone spending 1 hour while keeping at 80° C. After completion of the dropwise addition, this was stirred for 30 minutes and then the reaction solution was distilled under a reduced pressure to obtain 182 g of piperitenone. Yield 62%.

Synthesis Example 3

Synthesis of Piperitenone Using Methyl Vinyl Ketone

A 688 ml (6.0 mol) portion of mesityl oxide was put into a one liter capacity four neck flask and mixed with 13.82 g (0.1 mol) of potassium carbonate and 2.28 g (10 mmol) of benzyltriethylammonium chloride, and the mixture was heated to 80° C. To this was added dropwise 166.48 ml (2.0 mol) of methyl vinyl ketone spending 1 hour while keeping at 80° C. After completion of the dropwise addition, this was stirred for 30 minutes and then the reaction solution was distilled under a reduced pressure to obtain 186 g of piperitenone. Yield 62%.

EXAMPLE 1

Synthesis of Pulegone

A 100 ml capacity autoclave was charged with 3 g (20 mmol) of piperitenone, 2.5 mg (0.005 mmol) of [Rh(cod)Cl]$_2$, 7.3 mg (0.01 mmol) of (S)-DM-BINAP (2,2'-bis(di-3,5-xylylphosphino)-1,1'-binaphthyl), 4.3 mg (0.01 mmol) of HexPh$_3$PBr and 9 ml of THF, and the reaction was carried out at 50° C. for 18 hours under a hydrogen pressure of 3 MPa. The conversion ratio was 92% when measured by a gas chromatography. The product contained 90.1% of pulegone, 1.03% of piperitone, 0.9% of menthone and 0.8% of isomenthone. Enantio-selectivity of pulegone was 97.0% ee.

EXAMPLE 2

Synthesis of Pulegone

When the hydrogenation reaction was carried out in the same manner as described in Example 1 except that 2.3 mg (0.01 mmol) of BnEt$_3$NCl was used instead of HexPh$_3$PBr, the conversion ratio was 90.4%. The product contained 90.5% of pulegone, 1.0% of piperitone, 0.7% of menthone and 0.7% of isomenthone. Enantio-selectivity of pulegone was 95.7% ee.

EXAMPLE 3

Synthesis of Pulegone

When the hydrogenation reaction was carried out in the same manner as described in Example 1 except that 7.4 mg (0.01 mmol) of (S)-DM-H$_8$-BINAP (2,2'-bis(di-3,5-xylylphosphino)-5,5',6,6',7,7',8,8'-octahydro-1,1'-binaphthyl) was used instead of (S)-DM-BINAP, the conversion ratio was 93.5%. The product contained 87.3% of pulegone, 0.9% of piperitone, 2.7% of menthone and 1.9% of isomenthone. Enantio-selectivity of pulegone was 97.4% ee.

EXAMPLE 4

Synthesis of Pulegone

A 100 ml capacity autoclave was charged with 3 g (20 mmol) of piperitenone, 1.6 mg (0.004 mmol) of [Rh(cod)$_2$]BF$_4$, 2.9 mg (0.004 mmol) of (S)-DM-BINAP, 1.7 mg (0.004 mmol) of HexPh$_3$PBr and 9 ml of THF, and the reaction was carried out at 50° C. for 18 hours under a hydrogen pressure of 3 MPa. The conversion ratio was 92.6% when calculated. The product contained 84% of pulegone, 1.5% of piperitone, 1.9% of menthone and 1.8% of isomenthone. Enantio-selectivity of pulegone was 97.4% ee.

EXAMPLE 5

Synthesis of Pulegone

A 100 ml capacity autoclave was charged with 3 g (20 mmol) of piperitenone, 1.0 mg (0.002 mmol) of [Rh(cod)Cl]$_2$, 2.9 mg (0.004 mmol) of (S)-DM-BINAP, 1.7 mg (0.004 mmol) of HexPh$_3$PBr and 9 ml of acetone, and the reaction was carried out at 50° C. for 18 hours under a hydrogen pressure of 3 MPa. The conversion ratio was 99.2% when calculated. The product contained 88.3% of pulegone, 2.5% of piperitone, 2.5% of menthone and 1.9% of isomenthone. Enantio-selectivity of pulegone was 96.0% ee.

EXAMPLE 6

Synthesis of Pulegone

A 100 ml capacity autoclave was charged with 3 g (20 mmol) of piperitenone, 1.6 mg (0.004 mmol) of [Rh(cod)$_2$]OCOC$_3$F$_7$, 4.7 mg (0.004 mmol) of (S)-DTBM-SEGPHOS ((5,6),(5',6')-bis(methylenedioxy)biphenyl-2,2'-diyl)bis(di-3,5-di-tert-butyl-4-methoxyphenylphosphine), 1.7 mg (0.004 mmol) of HexPh$_3$PBr and 9 ml of THF, and the reaction was carried out at 50° C. for 18 hours under a hydrogen pressure of 3 MPa. The conversion ratio was 95.5% when calculated. The product contained 89.2% of pulegone, 2.4% of piperitone, 2.0% of menthone and 2.4% of isomenthone. Enantio-selectivity of pulegone was 98.1% ee.

EXAMPLE 7

Synthesis of Pulegone

A 500 ml capacity autoclave was charged with 150 g (1 mol) of piperitenone, 18.6 mg (0.04 mmol) of [Rh(cod)$_2$]PF$_6$, 47.2 mg (0.04 mmol) of (S)-DTBM-SEGPHOS, 14.8 mg (0.02 mmol) of BrPPh$_3$(CH$_2$)$_4$PPh$_3$Br and 7.5 ml of ethyl acetate, and the reaction was carried out at 50° C. for 20 hours under a hydrogen pressure of 3 Mpa. After completion of the reaction, hydrogen was purged, the reaction solution was concentrated and then distillation was carried out under a reduced pressure to obtain 136.8 g of pulegol. The yield was 90%.

EXAMPLE 8

Synthesis of Pulegol

A 100 ml capacity autoclave was charged with 3.04 g (20 mmol) of pulegone, 19.1 mg (0.02 mmol) of RuCl$_2$(PPh$_3$)$_3$, 0.2 M 1,3-diaminopropane 2-propanol solution (0.2 ml), 0.2 M potassium hydroxide 2-propanol solution (1.0 ml) and 2-propanol (14 ml), and the mixture was stirred at 25° C. for 3 hours under a hydrogen pressure of 2 MPa. After completion of the reaction, hydrogen was purged, the reaction solution was concentrated and then distillation was carried out under a reduced pressure to obtain 2.61 g of pulegol. The yield was 85%.

EXAMPLES 9 TO 12

Synthesis of Pulegol

Hydrogenation of pulegone was carried out under different conditions. The results are shown in Table 1. In this connection, the term 6:6' in the table means compound of formula (6):compound of formula (6'). Regarding the Ru-cat. in the Examples, $RuCl_2(PPh_3)_3$ (Example 9), $Ru_2Cl_4$((S)-tol-binap)$_2$(NEt$_3$) (Example 10), $RuCl_2[(o-tolyl)_3P]_2$(diaminoethane) (Example 11) and $RuCl_2$(bpbp)(diaminoethane) (Example 12) were used.

TABLE 1

| | s/c | Diamine | Hydrogen pressure (Mpa) | Temp. (° C.) | Time (h) | Conv. (%) | 6:6' (%) |
|---|---|---|---|---|---|---|---|
| 9 | 1000 | diamino-propane | 3.0 | 25 | 15 | >99 | >99:1 |
| 10 | 1000 | diamino-propane | 3.0 | 25 | 17 | >99 | >99:1 |
| 11 | 1000 | — | 3.0 | 25 | 17 | >99 | >99:1 |
| 12 | 1000 | — | 3.0 | 25 | 15 | >99 | >99:1 |

EXAMPLE 13

Synthesis of Pulegol

A 200 ml capacity autoclave was charged with 30.4 g (200 mmol) of pulegone, 19.1 mg (0.02 mmol) of $RuCl_2(PPh_3)_3$(propanediamine), 44.9 mg (0.4 mmol) of t-BuOK and 2-propanol (15 ml), and the mixture was stirred at 30° C. for 18 hours while forcing 3 Mpa of hydrogen. After completion of the reaction, hydrogen was purged and the reaction solution was concentrated and distilled under a reduced pressure to obtain 30.2 g of pulegol. The yield was 98%.

EXAMPLE 14

Synthesis of Menthol

A 100 ml capacity autoclave was charged with 1.0 g (6.5 mmol) of pulegol, 5% Pd-carbon (20 mg) and ethyl acetate (5 ml), and the mixture was stirred at 60° C. for 5 hours under a hydrogen pressure of 2 Mpa. After completion of the reaction, the reaction solution was cooled to room temperature and concentrated. A 0.99 g portion of a mixture of menthol:neoisomenthol=91:9 was obtained. The yield was 90%.

EXAMPLES 15 to 22

Synthesis of Menthol

Hydrogenation of pulegol was carried out under different conditions. The results are shown in Table 2. In this connection, the term 7:7" in the table means compound of formula (7):compound of formula (7').

TABLE 2

| Example | Catalyst | wt % | Sov. | MPa | ° C. | Time | Conv. | 7:7" | 7 + 7" |
|---|---|---|---|---|---|---|---|---|---|
| 15 | 5% Pd-C | 1.0 | Tol. | 3 | 80 | 2 hr | 100 | 95:5 | 57.5 |
| 16 | 5% Pd-C | 1.0 | Tol. | 3 | 50 | 2 hr | 100 | 94:6 | 45.1 |
| 17 | 5% Pd-C | 1.0 | — | 3 | 50 | 1 hr | 100 | 96:4 | 53.1 |
| 18 | Ra-Ni | 1.0 | — | 3 | 80 | 3 hr | 100 | 73:27 | 83.6 |
| 19 | 5% Pd-Al$_2$O$_3$ | 1.0 | — | 3 | 50 | 3 hr | 100 | 82:18 | 74.0 |
| 20 | 5% Pd-SiAlO$_4$ | 0.5 | — | 3 | 50 | 16 hr | 100 | 90:10 | 69.6 |
| 21 | 5% Rh-C | 1.0 | MeOH | 3 | 80 | 6 hr | 100 | 85:15 | 40.2 |
| 22 | 5% Ru-C | 0.5 | — | 3 | 50 | 16 hr | 100 | 60:40 | 70.8 |

EXAMPLE 23

Synthesis of Menthol

A 100 ml capacity autoclave was charged with 3.1 g (20 mmol) of pulegol, 6.2 mg (0.01 mmol) of Ru(OAc)$_2$(dppe) and methanol (3 ml), and the mixture was stirred at 50° C. for 18 hours while forcing 3 Mpa of hydrogen. After completion of the reaction, the reaction solution was cooled to room temperature and concentrated. A 3.1 g portion of a mixture of menthol:neomenthol:neoisomenthol=96:1.7:2.3 was obtained. The yield was 95.5%.

EXAMPLES 24 TO 33

Synthesis of Menthol

Hydrogenation of pulegol was carried out under us conditions. The results are shown in Table 3.

TABLE 3

| Example | Catalyst | Conversion ratio | 7:7':7" | 7 + 7' + 7" |
|---|---|---|---|---|
| 24 | Ru(OAc)$_2$((S)-dm-binap) | 100 | 90:3:7 | 93.9 |
| 25 | Ru(OAc)$_2$((R)-dm-binap) | 99.5 | 77:3:20 | 88.4 |
| 26 | Ru(OAc)$_2$((R)-tol-binap) | 100 | 88:2:10 | 93.0 |
| 27 | RU(OAc)$_2$((R)-H$_8$-binap) | 100 | 82:2:16 | 91.8 |
| 28 | Ru(OAc)$_2$((S)-segphos) | 45.2 | 81:6:13 | 33.5 |
| 29 | Ru(OAc)$_2$(PPh$_3$)$_2$ | 38.1 | 77:9:14 | 19.5 |
| 30 | Ru(OAc)$_2$(dppb) | 99.6 | 87:2:11 | 90.3 |
| 31 | Ru(OAc)$_2$(1,2-bis(diphenylphosphine)benzene) | 99.2 | 94:2:4 | 90.7 |
| 32 | Ru(OCO-t-Bu)$_2$(dppe) | 84.6 | 95:2:3 | 76.7 |
| 33 | Ru(OCOPh)$_2$(dppe) | 99.8 | 95:2:3 | 91.2 |

While the invention has been described in detail and with reference to specific embodiments thereof, it will be apparent to one skilled in the art that various changes and

What is claimed is:

1. A method for producing 1-menthol represented by a formula (7),

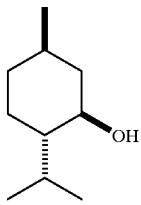
(7)

which comprises:

hydrogenation of piperitenone represented by a formula (1)

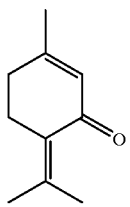
(1)

with a complex of an optically active phosphine represented by a general formula (2)

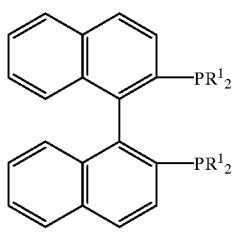
(2)

wherein $R^1$ represents an aryl group which may have a substituent group or a cycloalkyl group having from 3 to 8 carbon atoms and a transition metal, or a complex of an optically active phosphine represented by a general formula (3)

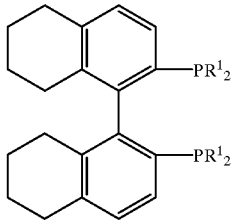
(3)

wherein $R^1$ represents an aryl group which may have a substituent group or a cycloalkyl group having from 3 to 8 carbon atoms and a transition metal, or a complex of an optically active phosphine represented by a general formula (4)

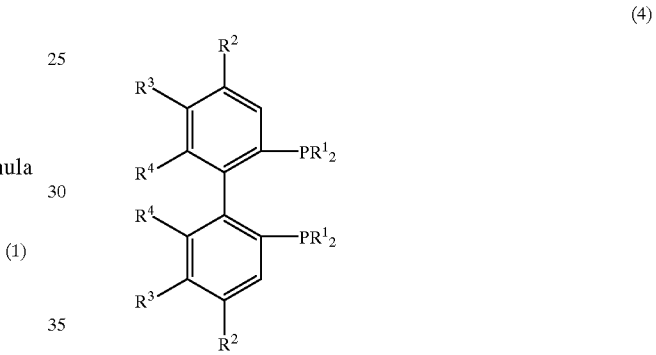
(4)

wherein $R^1$ represents an aryl group which may have a substituent group or a cycloalkyl group having from 3 to 8 carbon atoms, $R^2$ represents hydrogen atom or a lower alkyl group having from 1 to 4 carbon atoms, $R^3$ represents hydrogen atom, methyl group, methoxy group or a halogen atom, and $R^4$ represents methyl group or methoxy group, or $R^3$ and $R^4$ together form methylenedioxy group and a transition metal, thereby producing pulegone represented by a formula (5),

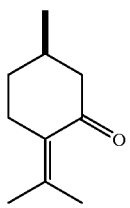
(5)

hydrogenation of the resulting pulegone with a ruthenium-phosphine-amine complex in the presence of a base, thereby obtaining pulegol represented by a formula (6)

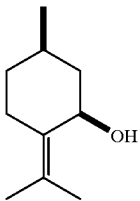

(6)

and further hydrogenation of the pulegol with a transition metal catalyst.

2. The method for producing 1-menthol according to claim 1, wherein the transition metal in the complex of an optically active phosphine represented by a general formula (2), (3) or (4) and a transition metal in the step of hydrogenating the piperitenone represented by a formula (1) to the pulegone represented by a formula (5) is selected from the group consisting of rhodium, iridium and ruthenium.

3. The method for producing 1-menthol according to claim 1, wherein the hydrogenation reaction is carried out by adding an ammonium salt, a phosphonium salt or an alkali metal salt to the complex of an optically active phosphine represented by a general formula (2), (3) or (4) and a transition metal in the step of hydrogenation of the piperitenone represented by a formula (1) to the pulegone represented by a formula (5).

4. The method for producing 1-menthol according to claim 2, wherein the hydrogenation reaction is carried out by adding an ammonium salt, a phosphonium salt or an alkali metal salt to the complex of an optically active phosphine represented by a general formula (2), (3) or (4) and a transition metal in the step of hydrogenation of the piperitenone represented by a formula (1) to the pulegone represented by a formula (5).

5. The method for producing 1-menthol according to claim 1, wherein the ruthenium-phosphine-amine complex which selectively hydrogenates carbonyl of pulegone in the step of hydrogenation of the pulegone represented by a formula (5) to the pulegol represented by a formula (6) is an achiral phosphine diamine ligand.

6. The method for producing 1-menthol according to claim 2, wherein the ruthenium-phosphine-diamine complex which selectively hydrogenates carbonyl of pulegone in the step of hydrogenation of the pulegone represented by a formula (5) to the pulegol represented by a formula (6) is an achiral phosphine diamine ligand.

7. A method for producing pulegone represented by a formula (5)

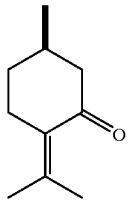

(5)

which comprises hydrogenation of piperitenone represented by a formula (1)

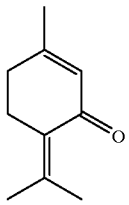

(1)

with a complex of an optically active phosphine represented by a general formula (2)

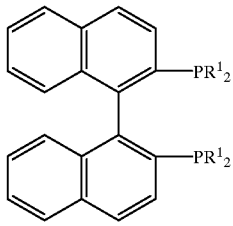

(2)

wherein $R^1$ represents an aryl group which may have a substituent group or a cycloalkyl group having from 3 to 8 carbon atoms
and a transition metal selected from the group consisting of rhodium, iridium and ruthenium,
or a complex of an optically active phosphine represented by a general formula (3)

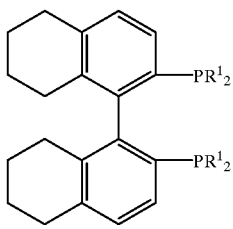

(3)

wherein $R^1$ represents an aryl group which may have a substituent group or a cycloalkyl group having from 3 to 8 carbon atoms
and a transition metal selected from the group consisting of rhodium, iridium and ruthenium,
or a complex of an optically active phosphine represented by a general formula (4)

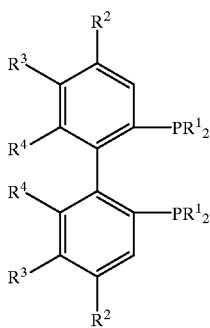

(4)

wherein $R^1$ represents an aryl group which may have a substituent group or a cycloalkyl group having from 3 to 8 carbon atoms, $R^2$ represents hydrogen atom or a lower alkyl group having from 1 to 4 carbon atoms, $R^3$ represents hydrogen atom, methyl group, methoxy group or a halogen atom, and $R^4$ represents methyl group or methoxy group, or $R^3$ and $R^4$ together form methylenedioxy group
and a transition metal selected from the group consisting of rhodium, iridium and ruthenium.

8. The method for producing pulegone according to claim 7, wherein the hydrogenation reaction is carried out by adding an ammonium salt, a phosphonium salt or an alkali metal salt to the complex of an optically active phosphine and a transition metal as defined in claim 7.

9. The method for producing 1-menthol according to claim 1, wherein the transition metal catalyst which selectively hydrogenates the olefin of pulegol in the step of hydrogenating the pulegol represented by a formula (6) to the 1-menthol represented by a formula (7) is a heterogeneous catalyst of palladium, iridium, rhodium, ruthenium, nickel, osmium or platinum.

10. The method for producing 1-menthol according to claim 1, wherein the transition metal catalyst which selectively hydrogenates the olefin of pulegol in the step of hydrogenation of the pulegol represented by a formula (6) to the 1-menthol represented by a formula (7) is a homogeneous catalyst in the form of a ruthenium-phosphine- dicarboxylate complex.

11. The method for producing 1-menthol according to claim 1, wherein the base in the step of hydrogenation of the pulegone represented by a formula (5) to the pulegol represented by a formula (6) is selected from the group consisting of an alkali metal compound or alkaline earth metal compound.

* * * * *